US00PP24461P2

(12) United States Plant Patent
Kanazawa

(10) Patent No.: US PP24,461 P2
(45) Date of Patent: May 13, 2014

(54) ***SENECIO* PLANT NAMED 'SUNSENEKABAPI'**

(50) Latin Name: ***Senecio cruentus*×*Senecio heritierii***
Varietal Denomination: Sunsenekabapi

(75) Inventor: Yoshiki Kanazawa, Kawachi-machi (JP)

(73) Assignee: Suntory Flowers Ltd., Tokyo (JP)

( * ) Notice: Subject to any disclaimer, the term of this patent is extended or adjusted under 35 U.S.C. 154(b) by 155 days.

(21) Appl. No.: 13/506,502

(22) Filed: Apr. 23, 2012

(51) Int. Cl.
*A01H 5/00* (2006.01)

(52) U.S. Cl.
USPC ..... Plt./480

(58) Field of Classification Search
USPC ..... Plt./480
See application file for complete search history.

*Primary Examiner* — June Hwu
(74) *Attorney, Agent, or Firm* — C. A. Whealy

(57) ABSTRACT

A new and distinct cultivar of *Senecio* plant named 'Sunsenekabapi', characterized by its upright and mounded plant habit; freely branching growth habit; freely flowering habit; and large daisy-type inflorescences with purple violet-colored ray florets and dark red purple-colored disc florets.

1 Drawing Sheet

Botanical designation: *Senecio cruentus*×*Senecio heritierii.*

Cultivar denomination: 'SUNSENEKABAPI'.

BACKGROUND OF THE INVENTION

The present invention relates to a new and distinct cultivar of *Senecio* plant, botanically known as *Senecio cruentus*× *Senecio heritierii*, and hereinafter referred to by the name 'Sunsenekabapi'.

The new *Senecio* plant is a product of a planned breeding program conducted by the Inventor in Kawachi-machi, Inashiki-gun, Ibaraki, Japan. The objective of the breeding program is to create new upright and mounding *Senecio* plants with numerous attractive inflorescences.

The new *Senecio* plant originated from an open pollination in March, 2007 of a proprietary selections of *Senecio cruentus*×*Senecio heritieri* identified as code number BW20, not patented, as the female, or seed, parent with an unknown proprietary selection of *Senecio cruentus*×*Senecio heritieri* as the male, or pollen, parent. The new *Senecio* plant was discovered and selected by the Inventor as a single flowering plant within the progeny of the stated open-pollination in a controlled environment in Kawachi-machi, Inashiki-gun, Ibaraki, Japan in January, 2008.

Asexual reproduction of the new *Senecio* plant by terminal cuttings in a controlled greenhouse environment in Kawachi-machi, Inashiki-gun, Ibaraki, Japan since January, 2008 has shown that the unique features of this new *Senecio* plant are stable and reproduced true to type in successive generations.

SUMMARY OF THE INVENTION

Plants of the new *Senecio* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunsenekabapi'. These characteristics in combination distinguish 'Sunsenekabapi' as a new and distinct *Senecio* plant:

1. Upright and mounded plant habit.
2. Freely branching growth habit.
3. Freely flowering habit.
4. Large daisy-type inflorescences with purple violet-colored ray florets and dark red purple-colored disc florets.

Plants of the new *Senecio* can be compared to plants of the female parent selection. Plants of the new *Senecio* differ from plants of the female parent selection in the following characteristics:

1. Plants of the new *Senecio* are shorter than plants of the female parent selection.
2. Plants of the new *Senecio* have smaller inflorescences than plants of the female parent selection.
3. Plants of the new *Senecio* and the female parent selection differ in ray floret color as plants of the female parent selection have red-colored ray florets.

Plants of the new *Senecio* can be compared to plants of *Senecio cruentus*×*Senecio heritieri* 'Sunsenere', disclosed in U.S. Plant Pat. No. 12,162. In side-by-side comparisons conducted in Higashiomi, Shiga, Japan, plants of the new *Senecio* differed from plants of 'Sunsenere' in the following characteristics:

1. Plants ofthe new *Senecio* had smaller, more deeply serrated and darker green-colored leaves than plants of 'Sunsenere'.
2. Plants of the new *Senecio* and 'Sunsenere' differed in ray floret color as plants of 'Sunsenere' had purple-colored ray florets.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet comprises a side perspective view of a typical flowering plant of 'Sunsenekabapi' grown in a container.

The photograph at the bottom of the sheet is a close-up view of a typical flowering plant of 'Sunsenekabapi'.

DETAILED BOTANICAL DESCRIPTION

The aforementioned photographs, following observations and measurements describe plants grown in 15-cm containers during the winter in a polyethylene-covered greenhouse in Higashiomi, Shiga, Japan and under cultural practices which approximate those generally used in commercial *Senecio* production. During the production of the plants, day temperatures averaged 10° C. and night temperatures averaged 5° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Senecio cruentus*×*Senecio heritierii* 'Sunsenekabapi'.

Parentage:

*Female, or seed, parent.*—Proprietary selection of *Senecio cruentus*×*Senecio heritierii* identified as code number BW20, not patented.

*Male, or pollen, parent.*—Unknown proprietary selection of *Senecio cruentus*×*Senecio heritieri*, not patented.

Propagation:

*Type.*—Terminal vegetative cuttings.

*Time to initiate roots.*—About one week at 18° C. to 20° C.

*Time to produce a rooted young plant.*—About four weeks at 18° C. to 20° C.

*Root description.*—Fine, fibrous; white in color.

*Rooting habit.*—Freely branching.

Plant description:

*Plant form/growth habit.*—Upright and mounded plant habit; daisy-type inflorescences positioned above the foliar plane; freely branching habit; vigorous growth habit.

*Plant height.*—About 34.7 cm.

*Plant diameter.*—About 45 cm.

*Lateral branches.*—Length: About 19.8 cm. Diameter: About 3.9 mm. Internode length: About 1.6 cm. Strength: Strong. Texture: Sparsely pubescent. Color: Close to 144B tinted with close to 183A.

*Foliage description.*—Arrangement: Alternate, simple. Length: About 5.9 cm. Width: About 6.8 cm. Shape: Cordate. Apex: Acute. Base: Cordate. Margin: Palmately lobed; deeply serrate; undulate. Texture, upper surface: Sparsely pubescent. Texture, lower surface: Densely pubescent. Venation pattern: Pinnate; reticulate. Color: Developing and fully expanded leaves, upper surface: Close to N137B; venation, close to 144B. Developing and fully expanded leaves, lower surface: Close to 138C; venation, close to 144D. Petioles: Length: About 7.8 cm. Diameter: About 2.6 mm. Texture, upper and lower surfaces: Pubescent. Color, upper surface: Close to 144B tinted with close to 59A. Color, lower surface: Close to 144B.

Inflorescence description:

*Appearance.*—Large daisy-type inflorescences with narrowly elliptic-shaped ray florets; inflorescences arising from upper leaf axils and positioned above the foliar plane; disc and ray florets developing acropetally on a capitulum; inflorescences face upright and outwardly; freely flowering habit with about 100 inflorescences developing per plant.

*Fragrance.*—None detected.

*Natural flowering season.*—Plants of the new *Senecio* begin flowering about 22 weeks after planting; plants flower continuously from winter to late spring.

*Inflorescence longevity.*—Inflorescences last about two weeks on the plant; inflorescences persistent.

*Inflorescence bud.*—Height: About 8.2 mm. Diameter: About 5.8 mm. Shape: Globose. Color: Close to N78A.

*Inflorescence size.*—Diameter: About 7 cm. Depth (height): About 1 cm. Disc diameter: About 1 cm.

*Ray florets.*—Shape: Narrowly elliptic. Length: About 3.1 cm. Width: About 7.8 mm. Apex: Acute. Base: Obtuse. Margin: Entire. Texture, upper and lower surfaces: Smooth, glabrous. Number of ray florets per inflorescence: About 12 to 14 in a single whorl. Color: When opening, upper surface: Close to N81A. When opening, lower surface: Close to N80B. Fully opened, upper surface: Close to N81A; towards the base, close to N80B; color does not fade with development. Fully opened, lower surface: Close to N81C; towards the base, close to lighter than N78C.

*Disc florets.*—Shape: Tubular; apex dentate, five-pointed. Length: About 8.6 mm. Diameter: About 1.2 mm. Number of disc floret per inflorescence: About 100. Color, immature: Apex: Close to 72A. Mid-section: Close to 150D. Base: Close to 150B. Color, mature: Apex: Close to 72A. Mid-section: Close to 150D. Base: Close to 151B.

*Phyllaries.*—Quantity per inflorescence: About twelve in a single whorl. Length: About 7.7 mm. Width: About 1.8 mm. Shape: Narrowly elliptic. Apex: Acute. Base: Fused. Margin: Entire. Texture, upper and lower surfaces: Smooth, glabrous. Color, upper surface: Close to 144A. Color, lower surface: Close to 144B.

*Peduncles.*—Length: About 3.1 cm. Diameter: About 1.7 mm. Strength: Strong. Aspect: Upright to somewhat outwardly. Texture: Smooth, glabrous. Color: Close to 146B occasionally tinted with close to 183A.

*Reproductive organs.*—Androecium: Present on disc florets only. Anther shape: Ellipsoidal. Anther color: Close to N78A. Pollen amount: Scarce. Pollen color: Close to 6A. Gynoecium: Present on both ray and disc florets. Stigma shape: Bi-parted, curled. Stigma color: Close to N78A.

*Seeds and fruits.*—Seed and fruit development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunsenekabapi' as illustrated and described.

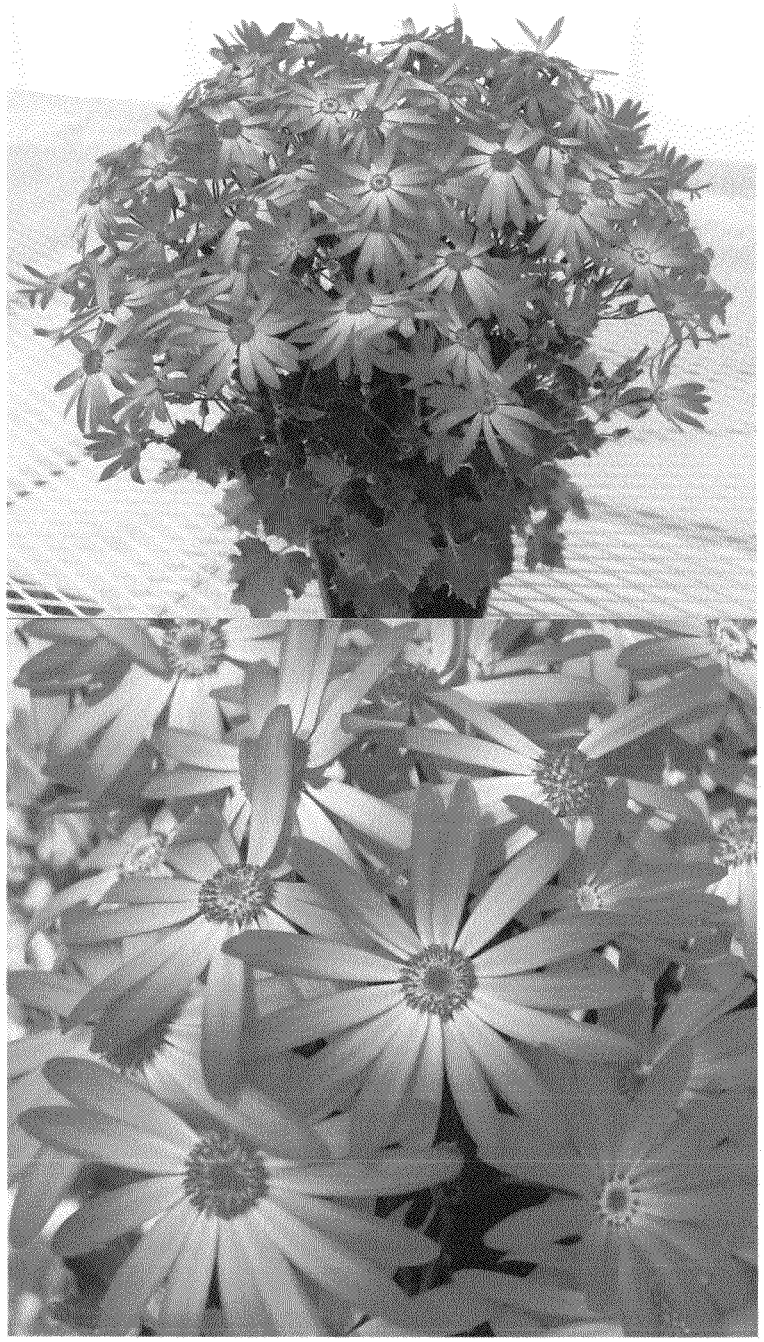

* * * * *